(12) United States Patent
Schranz et al.

(10) Patent No.: US 12,161,806 B2
(45) Date of Patent: Dec. 10, 2024

(54) VENTILATOR WITH AUTOMATIC DETECTION OF A FAULT IN A FLOW SENSOR, TAKING INTO ACCOUNT SPONTANEOUS BREATHING

(71) Applicant: Hamilton Medical AG, Bonaduz (CH)

(72) Inventors: Christoph Schranz, Bonaduz (CH); Dominik Wolf, Chur (CH); Dominik Novotni, Chur (CH)

(73) Assignee: Hamilton Medical AG, Bonaduz (CH)

( * ) Notice: Subject to any disclaimer, the term of this patent is extended or adjusted under 35 U.S.C. 154(b) by 1221 days.

(21) Appl. No.: 16/753,845

(22) PCT Filed: Sep. 24, 2018

(86) PCT No.: PCT/EP2018/075813
§ 371 (c)(1),
(2) Date: Apr. 6, 2020

(87) PCT Pub. No.: WO2019/068496
PCT Pub. Date: Apr. 11, 2019

(65) Prior Publication Data
US 2020/0282163 A1 Sep. 10, 2020

(30) Foreign Application Priority Data
Oct. 6, 2017 (DE) ...................... 10 2017 217 858.2

(51) Int. Cl.
*A61M 16/00* (2006.01)
*A61M 16/20* (2006.01)

(52) U.S. Cl.
CPC ...... *A61M 16/024* (2017.08); *A61M 16/0003* (2014.02); *A61M 16/0051* (2013.01);
(Continued)

(58) Field of Classification Search
CPC .............. A61M 16/024; A61M 16/022; A61M 16/021; A61M 16/00; A61M 16/0003;
(Continued)

(56) References Cited

U.S. PATENT DOCUMENTS

| 4,036,221 A | * | 7/1977 | Hillsman | A61M 16/00 128/204.23 |
| 8,196,575 B2 | | 6/2012 | Li et al. | |
| 2004/0211423 A1 | * | 10/2004 | Baecke | A61M 16/024 128/204.23 |

(Continued)

FOREIGN PATENT DOCUMENTS

| CN | 00998902 A | 7/2007 |
| CN | 100998902 A | 7/2007 |
| CN | 104162219 A | 11/2014 |
| DE | 10 2015 216 895 | 3/2017 |

(Continued)

OTHER PUBLICATIONS

Search Report issued in German Application No. 10 2017 217 858.2 on Sep. 24, 2018.
CN Office Action for CN 201880065261.8 dated Jan. 18, 2023, which corresponds to the present application.

*Primary Examiner* — Kendra D Carter
*Assistant Examiner* — Maap Ahmed Ellabib
(74) *Attorney, Agent, or Firm* — Tollefson IP

(57) ABSTRACT

The invention relates to a ventilator including a ventilation gas source, a ventilation tube assembly, a valve assembly, a flow sensor assembly comprising a distal flow sensor and a proximal flow sensor, a pressure sensor assembly for quantitatively detecting a gas pressure in the ventilation tube assembly a pressure-changing assembly for changing the gas pressure in the ventilation tube assembly and a control device which is designed at least to control the operation of the pressure-changing assembly on the basis of measurement signals from the proximal flow sensor, and on the basis of measurement signals from the proximal flow sensor and from the distal flow sensor, to infer the existence of a fault.

18 Claims, 6 Drawing Sheets

(52) U.S. Cl.
CPC ...... *A61M 16/0057* (2013.01); *A61M 16/204* (2014.02); *A61M 16/205* (2014.02); *A61M 2016/0027* (2013.01); *A61M 2016/003* (2013.01); *A61M 2205/332* (2013.01); *A61M 2205/3334* (2013.01)

(58) Field of Classification Search
CPC ................ A61M 16/20; A61M 16/205; A61M 2205/32; A61M 2205/3355; A61M 16/0057; A61M 16/0066; A61M 16/0069; A61M 16/107; A61M 16/12; A61M 16/204; A61M 2016/0021; A61M 2016/0027; A61M 2016/0036; A61M 2016/0039; A61M 2205/3358; A61M 2205/505; A61M 2205/52; A61M 2230/10; A61M 2230/18; A61M 2230/60; A61M 2230/63; F04D 25/166; F04D 29/052; F04D 29/286
See application file for complete search history.

(56) References Cited

U.S. PATENT DOCUMENTS

| | | | |
|---|---|---|---|
| 2006/0130835 A1* | 6/2006 | Truschel | A61M 16/204 128/204.23 |
| 2007/0163579 A1* | 7/2007 | Li | A61M 16/0081 128/203.14 |
| 2007/0215146 A1* | 9/2007 | Douglas | A61M 16/06 128/200.24 |
| 2008/0257350 A1 | 10/2008 | Huang et al. | |
| 2014/0261410 A1 | 9/2014 | Sanchez et al. | |
| 2015/0040905 A1* | 2/2015 | Kulstad | A61M 16/10 128/204.23 |
| 2019/0192796 A1 | 6/2019 | Schranz et al. | |

FOREIGN PATENT DOCUMENTS

| | | |
|---|---|---|
| DE | 10 2017 217 859 | 8/2018 |
| WO | 03/055552 | 7/2003 |
| WO | 2017/037152 | 3/2017 |

* cited by examiner

VENTILATOR WITH AUTOMATIC DETECTION OF A FAULT IN A FLOW SENSOR, TAKING INTO ACCOUNT SPONTANEOUS BREATHING

CROSS-REFERENCE TO RELATED APPLICATIONS

This application is the National Stage of International Application No. PCT/EP2018/075813, filed on Sep. 24, 2018, which claims the benefit of German Application No. 10 2017 217 858.2, filed on Oct. 6, 2017. The entire contents of both applications are hereby incorporated herein by reference.

BACKGROUND OF THE INVENTION

The present invention relates to a ventilation apparatus for artificial ventilation of a patient, having
    a respiratory gas source;
    a ventilation conduit arrangement proceeding between the respiratory gas source and a patient-side proximal end;
    a valve arrangement encompassing an inhalation valve and an exhalation valve;
    a flow sensor arrangement for quantitative detection of a gas flow in the ventilation conduit arrangement, encompassing a distal flow sensor arranged farther from the patient-side end of the ventilation conduit arrangement, and a proximal flow sensor located closer to the patient-side end of the ventilation conduit arrangement;
    a pressure sensor arrangement for quantitative detection of a gas pressure of gas flowing in the ventilation conduit arrangement;
    a pressure modification arrangement for modifying the gas pressure of the gas flowing in the ventilation conduit arrangement; and having
    a control device that is embodied at least
        to control the operation of the pressure modification arrangement on the basis of measured signals of the proximal flow sensor, and
        to infer a fault in the proximal flow sensor as a function of measured signals of the proximal flow sensor and of the distal flow sensor.

A ventilation apparatus that is known on the market is, for example, the "SERVO-U" product of the Maquet company. This known ventilation apparatus uses a distal flow sensor in the interior of a ventilation device. The distal end of a ventilation hose arrangement of the ventilation conduit arrangement is connected to the ventilation device. The known ventilation apparatus furthermore uses a proximal flow sensor in the form of a hot wire anemometer in a Y-connection piece. On its side facing toward the respiratory gas source the Y-connection piece connects a hose pair, made up of an inhalatory ventilation hose and an exhalatory ventilation hose embodied separately from the inhalatory ventilation hose, to a ventilation conduit that is arranged on that side of the ventilation hose which faces toward the patient and leads to the patient. The operating instructions for this known ventilation apparatus indicate, without more detailed stipulation, that the outputs of internal pressure and flow sensors are compared with the measurement result of the proximal sensor in the Y-connection piece, and the proximal sensor is deactivated if a significant deviation is discerned between the values utilized for the comparison.

The "SERVO-U" ventilation apparatus is not of the species, however, since its control device is not embodied to control operation of the pressure modification arrangement on the basis of measured signals of the proximal flow sensor.

Ventilation apparatuses of the species that are known are, for example, ventilation apparatuses of the Applicant which are offered and sold on the market under the designations "Hamilton-S1," "Hamilton-G1," and "Hamilton-C3." They are capable of operating in the "adaptive pressure ventilation (APV)" mode made known by the Applicant, in which the control device modifies the pressure of the respiratory gas in the ventilation conduit arrangement, depending on the measured signal of the proximal flow sensor (i.e. depending on the detected proximal flow of the respiratory gas), in such a way that the gas volume administered to the patient reaches or maintains a predetermined setpoint or setpoint range. Other commercially usual designations for the APV mode of ventilation apparatuses of the Applicant are PC-CMVa and PC-IMV (each per Chatburn) or PRVC (pressure regulated volume control).

The control devices of the ventilation apparatuses of the species compare values of a respiratory gas volume which were ascertained from measured signals of the distal and proximal flow sensors, and infer a fault in the proximal flow sensor if the proximal respiratory gas volume ascertained on the basis of measured signals of the proximal flow sensor, and the distal respiratory gas volume ascertained from measured signals of the distal flow sensor, differ in a manner other than that which is expected or permissible for the respectively existing operating state. The difference in respiratory gas volumes which is expected or permissible depending on the operating state can be taken into account by way of threshold parameters or threshold characteristics diagrams in which at least one difference threshold value for fault identification is stored, in particular is stored as a function of other operating parameters, in a data memory of the control device.

A disadvantage of the known ventilation apparatus of the species, and of the fault detection system disclosed therein which is supported only by the measured signals of the flow sensors, is that while patients are being ventilated, even though functionality of the measurement technology exists, situations can occur in the ventilation apparatus which influence the measured signals of the distal and proximal flow sensors in such a way that a comparison thereof, or a comparison of values ascertained therefrom, results, without further actions, in a false-positive fault detection.

It must be stated first in principle that the respiratory gas flow value detected by the distal flow sensor, and/or the respiratory gas volume value ascertained therefrom, is/are always quantitatively greater than the corresponding flow value detected by the proximal flow sensor and/or the volume value ascertained therefrom. This is due on the one hand to elasticity in that portion of the ventilation conduit arrangement which is located between the distal and proximal flow sensors. A portion of the gas flow which is detected by the distal flow sensor serves to expand the elastic portions of the ventilation conduit arrangement and does not reach the proximal flow sensor. A further reason relates to leaks in the exhalation valve, because of which a portion of the total respiratory gas flow can flow as a cross-flow in a fluid-mechanical short-circuit from the inhalation valve to the exhalation valve, without reaching the patient or the proximal flow sensor. The gas flow portion lost for ventilation of a patient as a cross-flow is also detected by the distal, but not the proximal, flow sensor.

It has now been found that an actual impairment of the functionality of the proximal flow sensor due to liquid accumulating therein—whether as a condensate from the respiratory air or, alternatively or additionally, due to the patient's saliva or body secretions—results in a significant distortion of the detection result of the proximal flow sensor. More precisely, the influence of the liquid accumulating in the proximal flow sensor is usually that a higher respiratory gas flow is detected, and a higher respiratory gas volume is ascertained therefrom, than are actually present.

The distal flow sensor, which as a rule is always uninfluenced by liquid, continues to detect the correct respiratory gas flow, so that because of the faulty detection by the proximal flow sensor, the detected flow values of the two sensors, and likewise the volume values ascertained (as a rule, by integration over time) from the flow values, approach one another in magnitude.

Specifically, when the proximal respiratory gas volume is controlled or regulated by modifying the respiratory gas pressure, for example in the aforementioned "APV" operating mode, an increase in the detected proximal respiratory gas flow, and consequently in the respiratory gas volume ascertained therefrom, results, as a consequence of control or regulation, in a lowering of the respiratory gas pressure in order to lower the proximal flow value detected as being elevated, and/or the volume value ascertained therefrom as being elevated, back to its original target level.

The control device thus keeps the proximal respiratory gas volume, ascertained from the detected proximal respiratory gas flow, constant by decreasing the respiratory gas pressure. As a consequence of the decreased pressure of the respiratory gas, however, the flow detected by the distal flow sensor drops as does the volume ascertained therefrom, thus resulting once again in a quantitative convergence of the flux values detected by the distal and proximal flow sensors and/or of the volume values ascertained therefrom.

The quantitative convergence of the detected flow values, and/or of the volume values ascertained therefrom, of the distal and proximal flow sensors is thus, in most (but not all) cases, an indication of a proximal flow sensor whose functionality has been impaired. Even a small number of false-positive fault messages or alarms in the context of artificial ventilation of patients is, however, undesired.

The object of the present invention is therefore to refine ventilation apparatuses of the species in such a way that a fault in the proximal flow sensor can be identified with even greater certainty than before, and the above-described false-positive fault detections can be avoided.

SUMMARY OF THE INVENTION

This object is achieved by way of a ventilation apparatus of the kind recited initially in which the control device is embodied to infer, as a function of measured signals of the proximal flow sensor and of the distal flow sensor, a candidate fault in the proximal flow sensor, and to infer a fault in the proximal flow sensor only with a time delay after identification of the candidate fault, the control device being embodied to reject the candidate fault if, during a verification phase that begins with or after identification of the candidate fault, at least one rejection criterion, taking into account a degree of spontaneous respiration activity by the patient, for rejecting the candidate fault is met.

When a rejection criterion is met during a verification phase, the previously identified candidate fault can be rejected, so that the proximal flow sensor is assessed as being still working correctly and the control device does not initiate any further action, but instead continues to operate the ventilation apparatus in accordance with the selected operating mode.

Clinical experiments have shown that a situation that results in identification of a candidate fault, i.e. a quantitative decrease in the difference between the respiratory gas volumes ascertained on the basis of respiratory gas flow values measured by the distal flow sensor and by the proximal flow sensor, can also be produced by spontaneous respiration by the patient. As a result of an active breath initiated or triggered by the patient, the respiratory gas flow value measured by the proximal flow sensor, and/or the respiratory gas volume value ascertained therefrom, can be elevated as compared with the corresponding values of breaths triggered in exclusively mandatory fashion by the ventilation apparatus. As a consequence thereof, the control device will lower the pressure setpoint for inhalatory respiratory gas in the ventilation conduit arrangement in order to return the value measured by the proximal flow sensor, and/or the value ascertained therefrom, to its setpoint. As a result of the decreased respiratory gas pressure, the distal inhalatory respiratory gas flow measured at the internal flow sensor drops, as does the inhalatory respiratory gas volume ascertained therefrom, so that the quantitative difference between the respiratory gas flows measured by the distal flow sensor and by the proximal flow sensor, and/or the respiratory gas volumes respectively ascertained therefrom, decreases.

In order avoid a false-positive identification, initiated by spontaneous respiration or active breaths, of a fault in the proximal flow sensor by the control device, provision is therefore made according to the present invention that the at least one rejection criterion takes into account spontaneous respiration by the patient connected to the ventilation apparatus. For example, the at least one rejection criterion can be dependent on or can take into account a number of active breaths initiated by the patient. For purposes of the present invention, a "number" is also considered to be a proportion of active breaths in terms of a total number of active breaths.

The rejection criterion can be a predetermined rejection criterion, i.e. it can be previously stored in the control device or in a data memory interacting with the control device, and can be read out as necessary from the data memory. It is also conceivable, however, for the rejection criterion to be ascertained during operation of the ventilation apparatus depending on operating parameters of the ventilation apparatus and on patient data or patient parameters. The use of a predetermined rejection criterion is preferred. Such a rejection criterion is also to be considered "predetermined" for purposes of the present Application if it is ascertained by the control device, individually for the selected operating mode and/or for the patient being ventilated, depending on preset operating parameters of the ventilation apparatus and/or on present patient data, but is stored in a data memory after being ascertained and is available there for further use during ventilation operation. The statements made regarding the predetermined nature of the rejection criterion also apply to the predetermined nature of all other parameters mentioned in this Application.

What applies to the rejection criterion in terms of ascertaining and predetermining therefore also applies to the beginning and/or duration of the verification phase. The verification phase is preferably predetermined in terms of beginning and duration, but it is not to be excluded that its beginning and/or duration is ascertained individually for a identified candidate fault depending on the possible parameters recited previously (operating parameters of the ventilation apparatus and/or state parameters of the patient (patient data)).

The verification phase can be a phase indicated as a time period. The verification phase is preferably a number of breaths. A "breath" in this context is a respiration event of a patient, encompassing an inhalation event and an exhalation event, which extends between the initiation times (also referred to technically as "trigger times") of two immediately successive inhalation events and is repeated periodically in order to ventilate a patient.

Thanks to rejection of the candidate fault as soon as the at least one rejection criterion is met during the verification phase, a false-positive fault message or a false-positive alarm due to spontaneous respiration can be avoided at an early stage. The output of a fault message, which also includes an alarm, is therefore authorized by the control device only if no rejection criterion is met during the verification phase.

The verification phase can begin a predetermined delay time period or a predetermined delay number of breaths after identification of a candidate fault. Preferably the verification phase begins with identification of the candidate fault. When the verification phase is defined as a number of breaths, the verification phase preferably begins either immediately upon identification of the candidate fault or upon initiation (triggering) of the breath immediately following the breath in which the candidate fault was identified.

The accuracy with which a candidate fault is rejected again once it has been identified can be further increased by the fact that the control device is embodied to reject the candidate fault if at least one rejection criterion is met at the end of the verification phase. It is then possible to prevent, so to speak, a "false-positive" rejection of the candidate fault because one rejection criterion was randomly and only briefly met. It is thereby possible to ensure that once a candidate fault has been identified, a time span or a number of breaths is applied as a delay that is usually required in order to identify whether an operating situation that results in recognition of a candidate fault is in fact based on a malfunction of the proximal flow sensor or has another cause.

For maximally reliable avoidance of false-positive fault messages, the control device preferably uses not just one rejection criterion but instead a plurality of rejection criteria. The control device can be embodied to reject the candidate fault only if more than one rejection criterion is met during the verification phase and/or is met at the end of the verification phase.

In a preferred specific embodiment, the rejection criterion that takes into account at least one spontaneous breath can encompass:

a number of active breaths by the patient being ventilated with the ventilation apparatus which are initiated by the patient during the verification phase exceeds an active-breath threshold value.

The terms "spontaneous respiration" and "active breath" are used synonymously in the present Application, since both terms refer to a breath initiated or triggered by the patient.

In principle, the control device of the ventilation apparatus can be signal-transferringly coupled to a further data processing device, and can receive information regarding active breaths by the patient from the further data processing device. Preferably, however, the control device is as independent as possible from further data processing devices and is therefore embodied to identify an active breath.

In principle, numerous methods are known from the existing art for automatically distinguishing active breaths from mandatory breaths, and thus for identifying active breaths even during artificial ventilation. For that purpose, the ventilation apparatus can use a variety of sensors, or can be signal-transferringly coupled to a variety of sensors, in order to identify an active breath from the data transferred to the control device from the sensors, and optionally from interposed control or evaluation devices of the sensors and from evaluation thereof.

In the technical field of artificial ventilation, under the rubric of "assisted spontaneous breathing" (ASB), numerous ways are known for identifying active breaths initiated by the patient during artificial ventilation. These too can be utilized in the present case.

Particularly preferably, the control device is embodied to detect a time period detection value, which represents a time period between the initiation of a detected breath and the initiation of the breath immediately following initiation of the detected breath, as a breath duration of the detected breath. The control device is further embodied to compare the time period detection value with an operating time period value that represents a time period between the respective mandatory initiations of two immediately successive mandatory breaths initiated by the ventilation apparatus. This latter time period is a mandatory breath duration. The control device is furthermore embodied to identify the detected breath, on the basis of the time period comparison result, as an active breath. The term "detected breath" refers simply to that breath for which the control device is intended to identify whether it is an active or a mandatory breath.

With the proposed detection of an active breath on the basis of a comparison of the time period detection value with the operating time period value, the control device can identify whether the detected breath is an active or a mandatory breath without requiring, for that purpose, further sensors beyond the sensors already present on the ventilation apparatus. Because the active breath triggered by the patient can be triggered by the patient only when the breath has not already been triggered by the ventilation apparatus, a breath that has occurred immediately before an active breath usually has a shorter breath duration than the mandatory breath duration established at the ventilation apparatus.

Instead of the breath duration, the respiration frequency proportional to the reciprocal of the breath duration can also be used. This too represents the breath duration of a breath.

Alternatively or additionally, the control device can detect or identify a breath as an active breath if it is embodied to detect a time period detection value, which represents a time period between the initiation of a detected breath and the initiation of the breath immediately following the detected breath, as a breath duration of the detected breath. The control apparatus is further embodied to compare the detected value with a time period comparison value that represents an average value of breath durations averaged over a plurality of breaths. Lastly, the control device is embodied to identify the detected breath as an active breath on the basis of the time period comparison result.

As a rule, the detected breath follows the plurality of breaths over whose breath durations an average is calculated. The detected breath can also be part of the plurality of breaths over whose durations the average is calculated. The detected breath is then preferably the latest one in time of the plurality of breaths.

In principle, any type of average calculation can be utilized. Preferably, an arithmetic average is calculated. It can be weighted or not.

Clinical experiments have shown that the breath durations upon the onset of spontaneous respiration are shorter than the breath durations of mandatory breaths, and that, in particular, successive active breaths exhibit increasingly shorter breath durations. Breath durations that are becoming shorter are equivalent to respiratory frequencies that are becoming greater.

It is furthermore possible for the plurality of breaths that are utilized for calculating the average of breath durations always to be the same plurality of breaths for assessing several different detected breaths. The breaths utilized for comparison can always be the same breaths, so that the average needs to be calculated only once or at long time intervals.

Maximally accurate detection of active breaths with little susceptibility to error can be achieved by the fact that the time period comparison value reproduces a sliding average of breath durations over a predetermined number of breaths following one another until the detected breath. Once again, the detected breath can follow the last breath of the plurality of breaths utilized for calculation of the sliding average, or can be part of the plurality of breaths. Preferably, it is the latest in time of the plurality of breaths. The sliding average is preferably an arithmetic average that can be weighted but does not need to be weighted.

A sliding average, or any average, of breath durations is preferably calculated over a number from five to ten breaths, particularly preferably eight breaths. Particularly preferably, the breaths utilized for calculation of the average of breath durations are immediately successive to one another in time.

In addition or alternatively to utilization of a breath duration or a breath frequency in order to identify active breaths, the control device of the ventilation apparatus can also identify an active breath, without additional sensor equipment, on the basis of the pressure values, present in any case in the pressure sensor arrangement, of the respiratory gas pressure of respiratory gas flowing in the ventilation conduit arrangement. The technical reason for this is that as a rule, a higher respiratory gas flow is detected in the context of a first active breath than in the context of a mandatory breath, since the patient's activity is added to the mandatory ventilation. As a consequence thereof, the respiratory gas pressure of the subsequent breath becomes lowered in the context of the pressure regulation function relevant here for achieving a target flow or a target tidal volume. The control device of the ventilation apparatus can thus also identify a detected breath as an active breath by the fact that the control device is embodied to detect a gas pressure of gas flowing in the ventilation conduit arrangement, and to compare a gas pressure detected during a detected breath with the gas pressure detected during a preceding breath, the control device being embodied to identify the detected breath as an active breath on the basis of the pressure comparison result. The detected gas pressure is preferably a pressure of an inhalatory respiratory gas.

The preceding breath is preferably a breath immediately preceding the detected breath, although it is not to be excluded that at least one further breath is present between the preceding breath and the detected breath.

In order to increase the accuracy with which an active breath is identified, the control device of the ventilation apparatus is preferably embodied to perform both a time period comparison and a pressure comparison, the detected breath then being identified, or not, as an active breath on the basis of both the time period comparison result and the pressure comparison result.

Additionally or alternatively, the control device of the ventilation apparatus can be embodied to detect, during a detected breath, at least one value of an esophageal pressure and/or of a pleural pressure of the patient, and to identify the detected breath as an active breath on the basis of the at least one detected pressure value, further sensors in addition to the sensor arrangements recited earlier as constituents of the ventilation apparatus being necessary for this. The pleural pressure is often also referred to as "interpleural pressure."

As a rule, however, the spontaneous respiration exhibited by the patient during artificial ventilation is relevant for false-positive candidate fault identification only when a sufficient number of active breaths have occurred during the verification phase. The active breath threshold value above which a rejection criterion is considered to exist can therefore, as a predetermined active breath threshold value, be equal to at least 39% of the total number of breaths in the verification phase.

The active breath threshold value can in turn be determined individually during artificial ventilation of the patient or even during the verification phase on the basis of operating data of the ventilation apparatus and/or based on patient data, or can be stored in a memory as a predetermined threshold value. The active breath threshold value is preferably a predetermined threshold value.

Because the influence of spontaneous respiration during the verification phase on candidate fault identification by the control device becomes greater as the number of breaths that have been initiated or triggered by the patient him- or herself, rather than by the ventilation apparatus, increases, in a further preferred embodiment of the ventilation apparatus the active breath threshold value can preferably be equal to at least 45%, even more preferably at least 50%, of the total number of breaths in the verification phase.

When spontaneous respiration in the verification phase is identified but the active breath threshold value has not been reached, however, some uncertainty can occur in the evaluation of the apparatus-specific and/or patient-specific parameters detected by the control device. In order to eliminate or at least reduce that uncertainty, the control device can be embodied to extend the verification phase to include an additional verification phase when the number of active breaths ascertained during the predetermined verification phase is greater than zero and less than the predetermined active breath threshold value.

The additional verification phase can be ascertained from individually existing operating data and/or patient data, or can be a predetermined additional verification phase that is stored in a data memory that interacts with the control device. The duration of the extended verification phase is then equal to the duration of the original verification phase plus the duration of the additional verification phase.

Even when the verification phase has been extended to include the additional verification phase, the control device preferably applies the same at least one rejection criterion as in the original verification phase, i.e. the verification phase is simply extended, and no adaptation of the at least one rejection criterion occurs when the verification phase is extended.

In principle, the above-described rejection criterion that takes into account spontaneous respiration by the patient can be the only rejection criterion the meeting of which results in rejection of the candidate fault and thus in evaluation of a possibly critical operating state of the ventilation apparatus, in particular of the proximal flow sensor, as non-faulty. The accuracy with which a fault in the ventilation apparatus, in particular in the proximal flow sensor, is identified can be even further enhanced, however, by the fact that the at least one rejection criterion additionally encompasses:

a quantitative volume difference value, which indicates a difference between the distal gas volume ascertained by means of the distal flow sensor and the proximal gas volume ascertained by means of the proximal flow sensor during the same breath, lies within a volume difference value permissibility range; and/or a quantitative pressure difference value, which indicates a difference between the gas pressures detected by the pressure sensor arrangement during different breaths, lies within a pressure difference value permissibility range.

Once again, one or both of the permissibility ranges can be stored in predetermined fashion in a data memory that interacts with the control device, or can be ascertained individually as a function of operating data and/or patient data at the point in time at which the candidate fault is identified.

This is because the candidate fault is usually identified by the fact that the quantitative volume difference value lies outside a volume difference value permissibility range, and/or that the quantitative pressure difference value lies outside a pressure difference value permissibility range. The fact that the condition that has been met for identifying a candidate fault stops existing during the verification phase, or at least no longer exists at the end of the verification phase, can in that regard also serve as a rejection criterion.

The control device is preferably embodied in such a way that it immediately rejects the candidate fault if, during the verification phase (which includes the aforementioned extended verification phase), one or both difference values lie within the respectively associated difference value permissibility range; and that the candidate fault is not rejected until, at the end of the verification phase (which includes the extended verification phase), the total number of breaths lies above the active breath threshold value.

According to an advantageous refinement of the present invention, the control device of the ventilation apparatus proposed in the present Application is embodied specifically to control the operation of the pressure modification arrangement on the basis of measured signals of the proximal flow sensor in such a way that in the mandatory ventilation operating mode as intended, it controls the pressure modification arrangement to modify the gas pressure of the inhalatory respiratory gas flowing in the ventilation conduit arrangement, in accordance with the measured signal of the proximal flow sensor, in such a way that a gas volume value ascertained on the basis of the gas flow value detected by the proximal flow sensor lies within a predefined volume value range, preferably is substantially constant.

This relates to the "APV" ventilation operating mode known from the Applicant, which has already been explained above. The gas volume value can be ascertained, for example, from the measured signal, representing a gas flow, of the proximal flow sensor, by integration over time.

In principle, it is possible in this context to use a proximal flow sensor that operates according to any physical principle, provided it is capable of measuring the respiratory gas flow at the location where it is arranged. For example, the proximal flow sensor can encompass a hot wire anemometer. Preferably, however, the proximal flow sensor is a differential pressure sensor, the pressure sensor arrangement detecting at least one of the gas pressures detected at the differential pressure sensor as the gas pressure of gas flowing in the ventilation conduit arrangement, and the control device using that detected gas pressure to ascertain a candidate fault in the proximal flow sensor. The proximal flow sensor can thus also serve to detect the respiratory gas pressure in the ventilation conduit arrangement.

BRIEF DESCRIPTION OF THE DRAWING FIGURES

In order to protect the patient from incorrect ventilation, the control device of the ventilation apparatus is preferably embodied to perform a control action on the ventilation apparatus when it infers a fault in the proximal flow sensor. One such control action can be the output of a fault message, including an alarm. This can also occur remotely from the installation location of the ventilation apparatus, for example via radio signals, at a location at which caregivers are present or available. The control device can also be embodied to continue artificial ventilation of the patient after identification of the fault, using operating parameters that were used at a predetermined point in time, or within a predetermined time period, before identification of the candidate fault. An auxiliary ventilation mode of this kind can, of course, be maintained for only a short time. It can nevertheless thereby be possible to ventilate the patient using operating parameters that are more correct than ones based on what is currently being supplied by the faulty proximal flow sensor. The time for such an emergency operating mode is limited by the simultaneous output of a fault message or an alarm.

The present invention will be explained in further detail below with reference to the appended drawings, in which.

Figure 1:
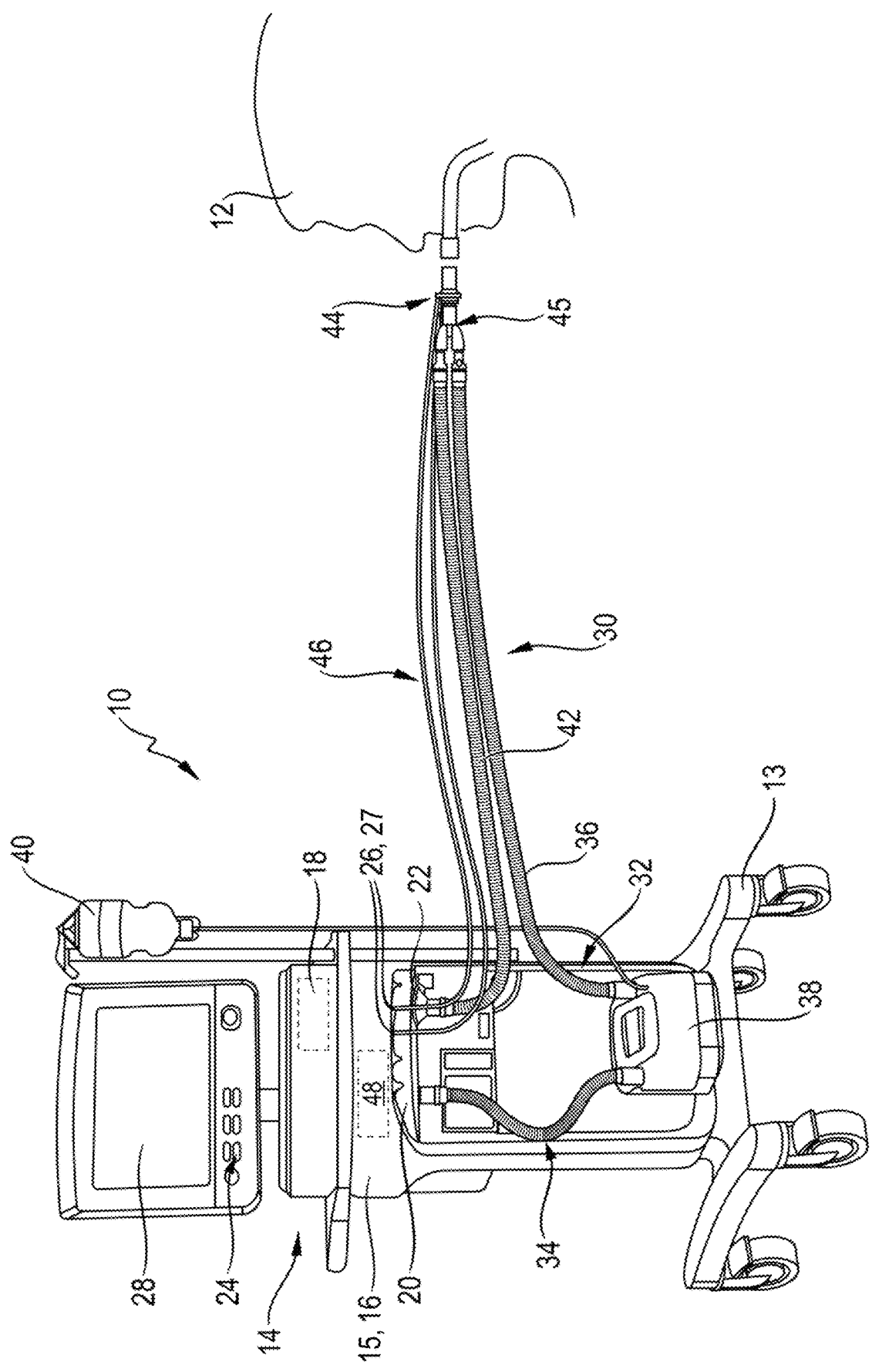
FIG. 1 depicts an embodiment of a ventilation apparatus according to the present invention.

In FIG. 1, an embodiment according to the present invention of a ventilation apparatus is labeled in general with the number 10. In the example depicted, ventilation apparatus 10 serves for artificial ventilation of a human patient 12.

Merely in the interest of completeness, be it noted that ventilation apparatus 10 according to the present invention, constituting a mobile ventilation apparatus 10, can be received on a rollable frame 13.

Ventilation apparatus 10 comprises a housing 14 in which a pressure modification arrangement 16 and a control device 18 (not visible from outside because the housing material is opaque) can be received.

Pressure modification arrangement 16 is constructed in a manner known per se and comprises a respiratory gas source 15 in the form of a pump, a compressor, or a fan, which are each controllable in adjustable-load fashion and therefore serve not only to introduce respiratory gas into the ventilation apparatus but also to modify the pressure of the respiratory gas that is introduced. Respiratory gas source 15 (gas source 15) can alternatively also be constituted by a pressure vessel that is connectable to housing 14 of ventilation apparatus 10. Pressure modification arrangement 16 can comprise gas source 15 and, if applicable, additionally (or, in the case of a pressurized gas reservoir constituting a gas source, alternatively) a reducing valve and the like. Ventilation apparatus 10 furthermore comprises, in a manner known per se, an inhalation valve 20 and an exhalation valve 22.

Control device 18 is usually implemented as a computer or microprocessor. It encompasses a memory device (not depicted in FIG. 1) so that data necessary for the operation of ventilation apparatus 10 can be stored and, as necessary, retrieved. In a network operating context, the memory device can also be located outside housing 14 and can be connected to control device 18 via a data transfer connection. The data transfer connection can be constituted by a cable link or a radio link. In order to prevent disruptions in the data transfer link from being able to affect the operation of ventilation apparatus 10, however, the memory device preferably is integrated into control device 18 or is at least received in the same housing 14 as the latter.

For inputting data into ventilation apparatus 10, or more precisely into control device 18, ventilation apparatus 10 comprises a data input 24 that is represented, in the example depicted in FIG. 1, by a keyboard. Alternatively or in addition to the keyboard that is depicted, control device 18 can receive data via a variety of data inputs, for example via a network lead, a radio link, or via sensor terminals 26 that will be discussed below in detail.

Ventilation apparatus 10 can comprise an output device 28, in the example depicted a screen, for outputting data to the therapist performing treatment.

For artificial ventilation, patient 12 is connected to ventilation apparatus 10, more precisely to pressure modification arrangement 16 in housing 14, via a ventilation conduit arrangement 30. Patient 12 is intubated for that purpose.

Ventilation conduit arrangement 30, through which fresh respiratory gas can be directed from gas source 15 and pressure modification arrangement 16 into the lungs of patient 12, comprises an inhalation hose 32 outside housing 14. Inhalation hose 32 can be interrupted, and can comprise a first inhalation sub-hose 34 and a second inhalation sub-hose 36 between which a conditioning device 38 can be provided for controlled humidification, and optionally also temperature control, of the fresh respiratory gas delivered to patient 12. Conditioning device 38 can be connected to an external liquid reservoir 40 by way of which water for humidification, or also a medication, for example to inhibit inflammation or to expand the airways, can be introduced into the respiratory gas. When the present ventilation apparatus 10 is used as an anesthesia ventilation apparatus, it is thereby possible to deliver volatile anesthetics to patient 12 in controlled fashion via ventilation apparatus 10. Conditioning device 38 ensures that the fresh respiratory gas is conveyed to patient 12 with a predetermined moisture content, if applicable with the addition of a medication aerosol, and at a predetermined temperature.

In addition to inhalation valve 20 already mentioned, ventilation conduit arrangement 30 comprises exhalation valve 22 and furthermore an exhalation hose 42 through which metabolized respiratory gas is discharged from the lungs of patient 12 into the atmosphere.

Inhalation hose 32 is coupled to inhalation valve 20, and exhalation hose 42 to exhalation valve 22. Only one of the two valves is respectively open at a given time for passage of a gas flow. Actuation control of valves 20 and 22 is likewise accomplished by control device 18.

During a respiration cycle, firstly exhalation valve 22 is closed and inhalation valve 20 is opened for the duration of the inhalation phase, so that fresh respiratory gas can be directed from housing 14 to patient 12. A flow of fresh respiratory gas is produced by pressure modification arrangement 16 by controlled elevation of the pressure of the respiratory gas. As a result of the pressure elevation, the fresh respiratory gas flows into the lungs of patient 12 where it expands the body region in the vicinity of the lungs, i.e. in particular the thorax, against the individual elasticity of the body parts in the vicinity of the lungs. The gas pressure in the interior of the lungs of patient 12 also rises as a result.

At the end of the inhalation phase, inhalation valve 20 is closed and exhalation valve 22 is opened. The exhalation phase begins. Because the gas pressure of the respiratory gas present in the lungs of patient 12 is elevated until the end of the inhalation phase, that gas flows into the atmosphere after exhalation valve 22 is opened, and the gas pressure in the lungs of patient 12 decreases as the flow duration proceeds. When the gas pressure in lungs 12 reaches a positive end expiratory pressure established at ventilation apparatus 10, i.e. a pressure slightly higher than atmospheric pressure, the exhalation phase is terminated with the closing of exhalation valve 22, and a further respiration cycle follows.

The so-called respiration tidal volume, i.e. the volume of respiratory gas for each breath, is delivered to patient 12 during the inhalation phase. The respiration tidal volume, multiplied by the number of respiration cycles per minute (i.e. multiplied by the respiration frequency), is equal to the volume per minute of artificial ventilation being carried out in the present case.

Ventilation apparatus 10, in particular control device 18, is preferably embodied to repeatedly update or ascertain, during ventilation operation, ventilation operating parameters that characterize the ventilation operation of ventilation apparatus 10, in order to ensure that ventilation operation is coordinated as optimally as possible at each point in time with the particular patient 12 being ventilated. Particularly advantageously, the determination of one or more ventilation operating parameters occurs at the respiration frequency, so that ventilation operating parameters that are current (and thus optimally adapted to patient 12) can be furnished for each respiration cycle.

Ventilation apparatus 10 is data-transferringly connected for that purpose to one or several sensors that monitor the status of the patient and/or operation of the ventilation apparatus.

One of these sensors is a proximal flow sensor 44 that, in a Y-connection piece 45, detects the respiratory gas flow existing there in ventilation conduit arrangement 30. Flow sensor 44 can be coupled by means of a sensor conduit arrangement 46 to sensor terminals 26 of control device 18. Sensor conduit arrangement 46 can, but does not need to, encompass electrical signal transfer lines. It can also comprise hose lines that transfer the gas pressure, existing on both sides of flow sensor 44 in the flow direction, to sensor terminals 26, where it is quantified by pressure sensors 27. Flow sensor 44 is depicted in the present instance as a differential flow sensor 44. Flow sensor 44 is preferably a flow sensor operating on the differential pressure principle, but can also be a flow sensor operating in accordance with a different physical principle.

Provided in housing 14 is a further flow sensor 48 that is referred to, because of its greater distance from patient 12 as compared with proximal flow sensor 44, as a "distal" flow sensor 48.

The measured signals of pressure sensors 27 can be used to implement a particularly advantageous operating mode that is known to specialists as "adaptive pressure ventilation," abbreviated APV. As a simplified explanation: the respiratory gas volume ascertained from the respiratory gas flow measured by proximal flow sensor 44 is modified, by modifying the pressure of the respiratory gas in ventilation conduit arrangement 30 using pressure modification arrangement 16, in such a way that the respiratory gas volume ascertained by means of proximal flow sensor 44 corresponds to a predefined setpoint or lies in a predefined setpoint range. The setpoint or setpoint range can be predefined by an attending physician by way of the input apparatus, or can be calculated from the patient data accessible to control device 18.

In the APV operating mode, a change in the respiratory gas volume ascertained by means of proximal flow sensor 44 therefore usually results in a change in the pressure of the respiratory gas in ventilation conduit arrangement 30.

Because of where it is installed in Y-connection piece 45, proximal flow sensor 44, unlike distal flow sensor 48, is also capable in principle of detecting the flow of exhalatory respiratory gas through exhalation hose 42.

Correct functioning of flow sensors 44 and 48 is essential for correct operation of ventilation apparatus 10 and thus for the health of patient 12.

It has been found during operation that specifically proximal flow sensor 44, because of its proximity to patient 12, is subject to a greater fault risk than distal flow sensor 48. For example, proximal flow sensor 44, through which exhaled respiratory gas also flows, is more highly stressed than distal flow sensor 48 by moisture contained in the respiratory gas. This applies all the more when, as in the present example of FIG. 1, distal flow sensor 48 is arranged upstream (in an inhalation direction) from conditioning device 38, and thus has substantially only dry inhalatory respiratory gas flowing through.

In order to monitor the operation of the flow sensor arrangement made up of proximal flow sensor 44 and distal flow sensor 48, control device 18 of ventilation apparatus 10 according to the present invention is embodied to be capable of promptly identifying a malfunction of the flow sensor arrangement.

Distal flow sensor 48 usually measures a quantitatively greater respiratory gas flow (which leads to a quantitatively greater respiratory gas volume ascertained therefrom) than proximal flow sensor 44, since distal flow sensor 48 is located closer to respiratory gas source 15 than is proximal flow sensor 44, and is thus subject to fewer gas-flow-reducing fault influences.

One such influence, for example, is the elasticity of ventilation conduit arrangement 30, in particular of inhalation hose 32. When inhalatory respiratory gas is introduced into that hose—said gas necessarily, due to the nature of the system, having a higher pressure than the ambient atmosphere—the introduced inhalatory respiratory gas performs work against the elasticity of inhalation hose 32 and expands it. This volume, enlarged by said expansion, of inhalation hose 32 receives respiratory gas that has flowed through distal flow meter 48 but no longer reaches patient 12 and proximal flow sensor 44 located directly upstream from him or her.

In addition, in many cases exhalation valve 22 does not seal hermetically, so that in the inhalation phase, a cross-flow occurs in a fluid-mechanical short-circuit between inhalation valve 20 and exhalation valve 22. Respiratory gas that flows through distal flow sensor 48 flows in this cross-flow, but it does not reach either proximal flow sensor 44 or patient 12, but firstly flows, in Y-connection piece 45, directly from inhalation hose 32 into exhalation hose 42.

The level of flow detection and, associated therewith, the volume ascertained by means of distal flow sensor 48 is thus quantitatively higher than the level of flow detection and, associated therewith, the volume ascertained by means of proximal flow sensor 44.

As has already been indicated above, moisture from the respiratory gas can condense in proximal flow sensor 44 and distort its measurement result. Based on existing experience, the result of a liquid-affected proximal flow sensor 44 is always a measured signal that indicates a quantitatively higher respiratory gas flow than the actual one. The consequence is a respiratory gas volume, ascertained therefrom, that has a quantitatively higher value than what was actually administered.

A proximal flow sensor 44 that is excessively stressed with liquid and is therefore sensing incorrectly can no longer regenerate itself, and must be replaced with a fault-free sensor unaffected by liquid in order to continue ensuring correct ventilation of patient 12.

A similar effect, i.e. an elevated proximal flow and consequently an elevated proximal respiratory gas volume, can, however, also occur for reasons other than excessive liquid stress on proximal flow sensor 44. For example, spontaneous respiration occurring during artificial ventilation can also modify the quantitative difference value between the distal respiratory gas flow measured by distal flow sensor 48 and the respiratory gas volume ascertained therefrom, and the proximal respiratory gas flow measured by proximal flow sensor 44 and the proximal respiratory gas flow ascertained therefrom, as compared with the difference value for exclusively mandatory ventilation.

Figure 2:
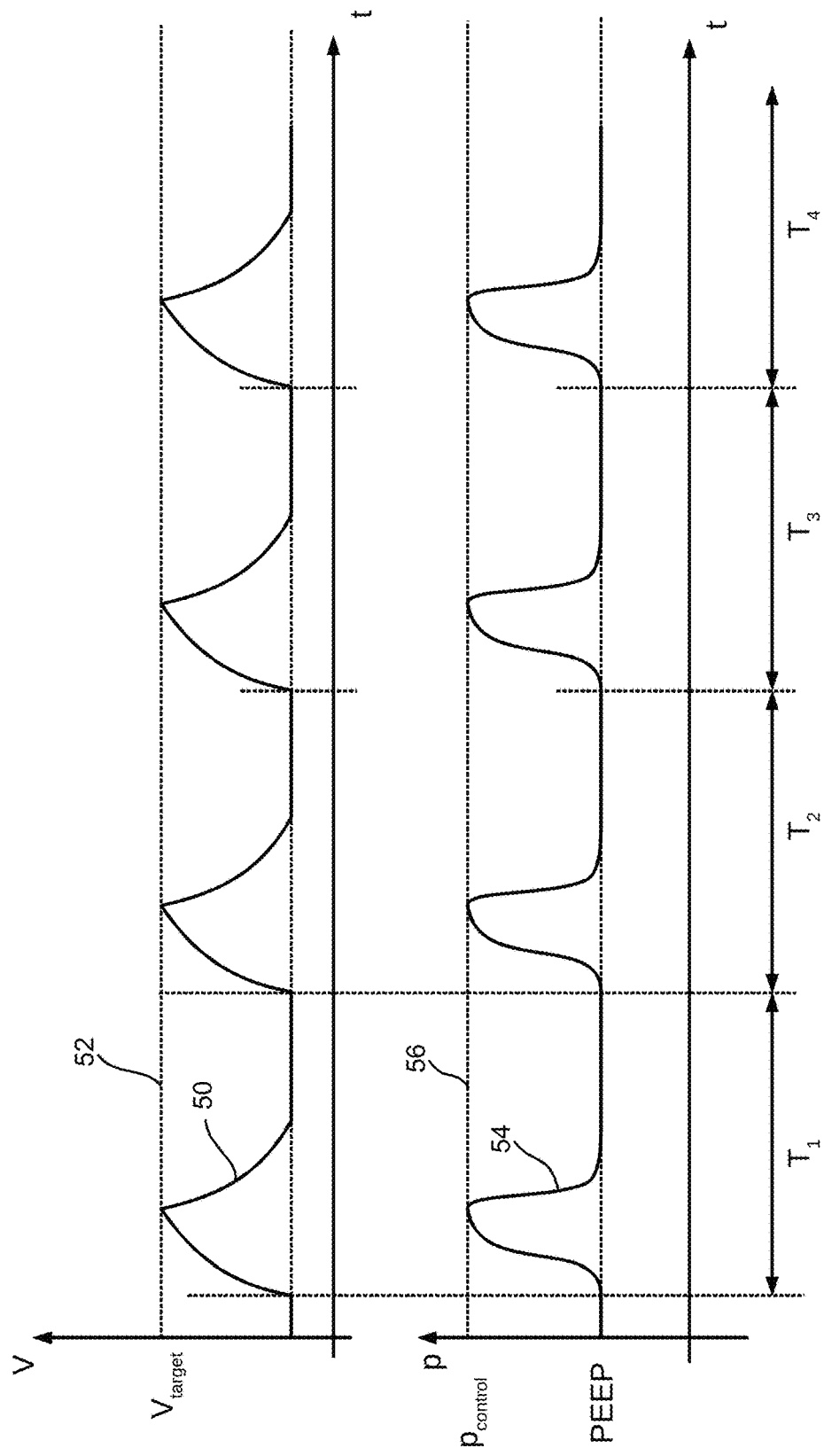
FIG. 2 depicts schematic curves as a function of time for a respiratory gas volume introduced into a patient's lungs and for the respiratory gas pressure in the ventilation conduit arrangement, in a context of exclusively mandatory ventilation.

Merely schematically for illustrative purposes, FIG. 2 shows in an upper diagram the respiratory gas mandatorily delivered to the artificially ventilated patient 12 as a function of time, the curve for respiratory gas volume as a function of time being labeled 50. A target definition of the tidal volume is depicted with the horizontal dashed line 52. Four successive breaths are plotted in FIG. 2. Below the respiratory gas volume as a function of time, the respiratory gas pressure as a function of time is depicted as curve 54, using the same time scale and again merely schematically. A maximum control pressure predefined by control device 18 of pressure modification arrangement 16 is labeled with the reference character 56. It is constant, in the exclusively mandatory artificial ventilation depicted in FIG. 2, over the four breaths that are depicted. For reasons that are known per se, control device 18 controls pressure modification device 16 in such a way that the respiratory gas pressure in the ventilation conduit arrangement does not drop below the positive end expiratory pressure (PEEP).

This ensures that when the respiratory gas pressure in ventilation conduit arrangement 30 reaches the control pressure $p_{control}$ predefined by control device 18, the tidal volume delivered to the patient corresponds to the target tidal volume $V_{target}$m. The tidal volume in accordance with the schematic curve 50 was ascertained using proximal flow sensor 44. When the respiratory gas volume delivered to the patient in a breath does not correspond sufficiently to the predefined target volume $V_{target}$, an elevated or reduced control pressure $p_{control}$ is defined by control device 18 for the next breath, so as thereby to keep the respiratory gas volume delivered to patient 12 as constant as possible for each breath.

A "breath" extends in this context from the point in time at which curve 50 of the respiratory gas volume as a function of time changes from its baseline toward higher values. The phase of increasing volume values corresponds to an inhalation phase; the phase of decreasing volume values corresponds to an exhalation phase. The time period between the beginnings of two inhalation phases immediately successive to one another in time is the breath duration $T_i$, where i=1 to 4 in FIG. 2.

Because the artificial ventilation depicted in FIG. 2 is occurring in exclusively mandatory fashion, i.e. exclusively initiated or triggered by ventilation apparatus 10, all the breath durations $T_1$ to $T_4$ shown in FIG. 2 have the same length.

Figure 3:
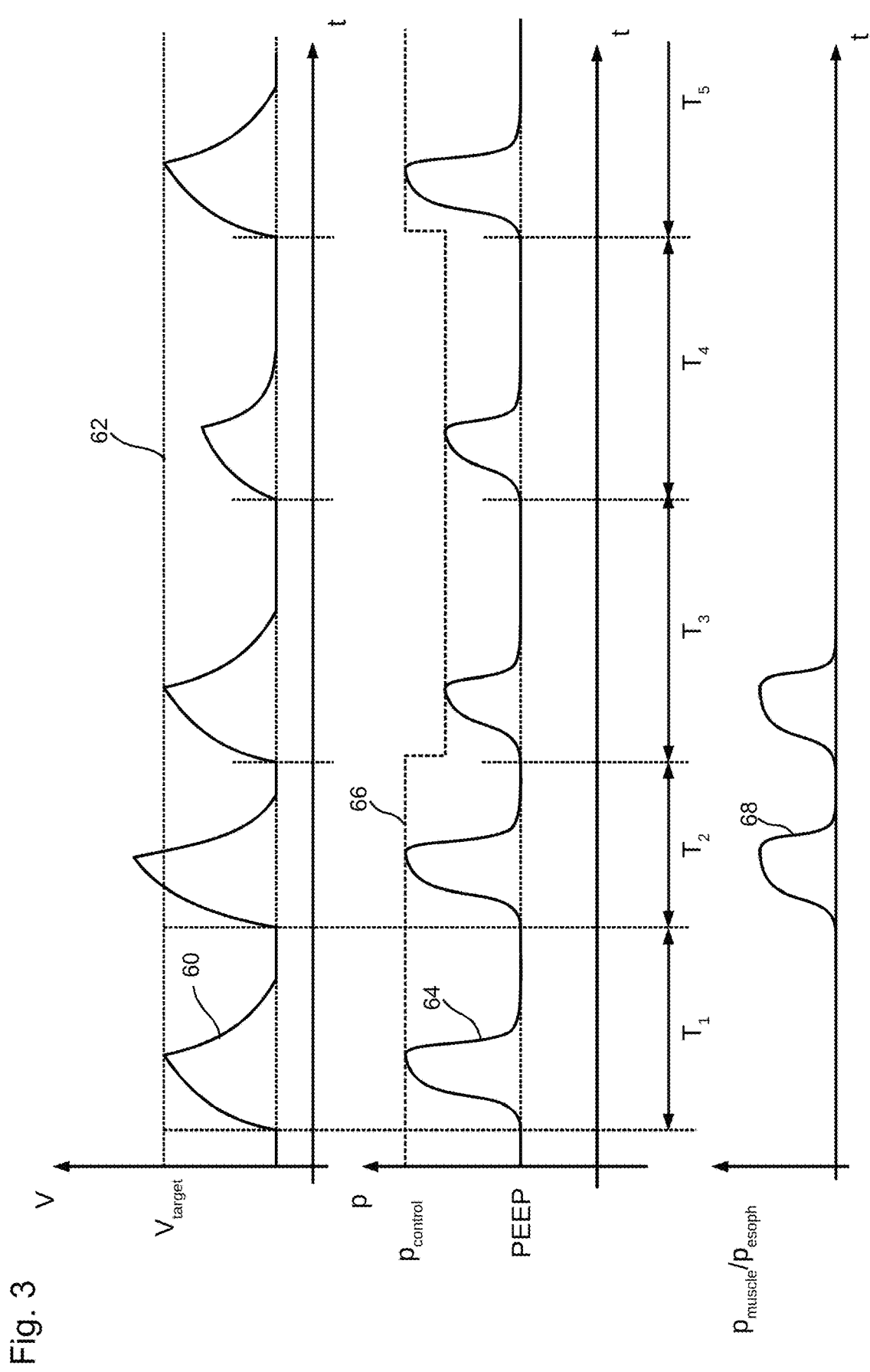
FIG. 3 depicts schematic curves as a function of time for respiratory gas volume, respiratory gas pressure, and an esophageal pressure, in a context of assisted spontaneous respiration.

FIG. 3 shows the same data curves as those depicted in FIG. 2, but with the occurrence of spontaneous respiration. Graphs and variables that are the same as in FIG. 2 are labeled with the same reference characters in FIG. 3 but incremented by 10.

FIG. 3 shows five breaths, or the respiratory gas volumes belonging to those breaths, immediately successive to one another in time, as a function of time, and the respiratory gas pressures in respiration conduit arrangement 30 as a function of time.

The first breath in FIG. 3 is a mandatory breath. Except for its shortened breath duration (explained in more detail below) it corresponds to the first breath in FIG. 2.

In FIG. 3, the second breath is an active breath that was initiated by the patient. Because patient 12 is independently aspirating respiratory gas in addition to the respiratory gas delivered to him or her via ventilation apparatus 10, in the second breath he or she receives a greater respiratory gas volume than provided for by control device 18 of ventilation apparatus 10. Proximal flow sensor 44 detects this. Control device 18 therefore lowers the control pressure $P_{control}$ for the next, third breath in order to return the respiratory gas volume delivered to the patient during a breath back to its setpoint $V_{target}$ (see target curve 62 in FIG. 3). Because the third breath of FIG. 3 is also an active breath, the return of the respiratory gas volume delivered to patient 12 back to the predefined target level is successful.

Because patient 12 is triggering the third breath, the breath duration $T_2$ of the second breath is shortened as compared with the predefined breath duration of a mandatory breath. The same also applies to the breath duration $T_1$ of the first breath, although this is not as clearly apparent in FIG. 3 as it is for the second breath.

The fourth breath is again an exclusively mandatory breath that is performed at the control pressure $p_{control}$, already in effect for the third breath, that resulted in the desired delivery of the target respiratory gas volume for the third breath. Because the patient's spontaneous respiration is absent in the fourth breath, however, the maximum pressure $p_{control}$ achieved by the respiratory gas during the inhalation phase is too low to deliver the target respiratory gas volume $V_{target}$ to the patient. The respiratory gas volume delivered to patient 12 in the fourth breath is accordingly too low, whereupon control device 18 controls pressure modification arrangement 16 to furnish a higher maximum respiratory gas pressure $p_{control}$ for the subsequent, fifth breath.

Respiration durations $T_1$, $T_2$, and $T_3$ have different lengths because of the spontaneous respiration in breaths 2 and 3. An exclusively mandatory breath immediately preceding an active breath is usually shortened in time with respect to an exclusively mandatory breath that is followed by a further exclusively mandatory breath. An exclusively mandatory breath immediately following an active breath in the context of the pressure regulation, as shown, for achieving a target tidal volume generally has too small a tidal volume or a tidal volume that is less than provided by control device 18. Thanks to these characteristic differences with respect to exclusively mandatory ventilation, control device 18 can identify individual breaths as active breaths of patient 12, without additional sensors, solely from the measurement signals from the flow sensors 44 and 48 that are present and pressure sensors 27 that are present.

As is evident from FIG. 3, however, alternatively or additionally an active breath can be identified by detecting the muscular pressure in the thorax region, or the esophageal pressure. Whereas with exclusively mandatory breaths no, or no appreciable, muscular or esophageal pressure occurs, curve 68 in FIG. 3 shows, in active breaths 2 and 3, an appreciable muscular or esophageal pressure, the detection of which, however, necessitates a further sensor that is otherwise not used for ventilation apparatus 10.

As will be explained below, the identification of active breaths plays a role in terms of avoiding false-positive fault messages in ventilation apparatus 10.

Figure 4:
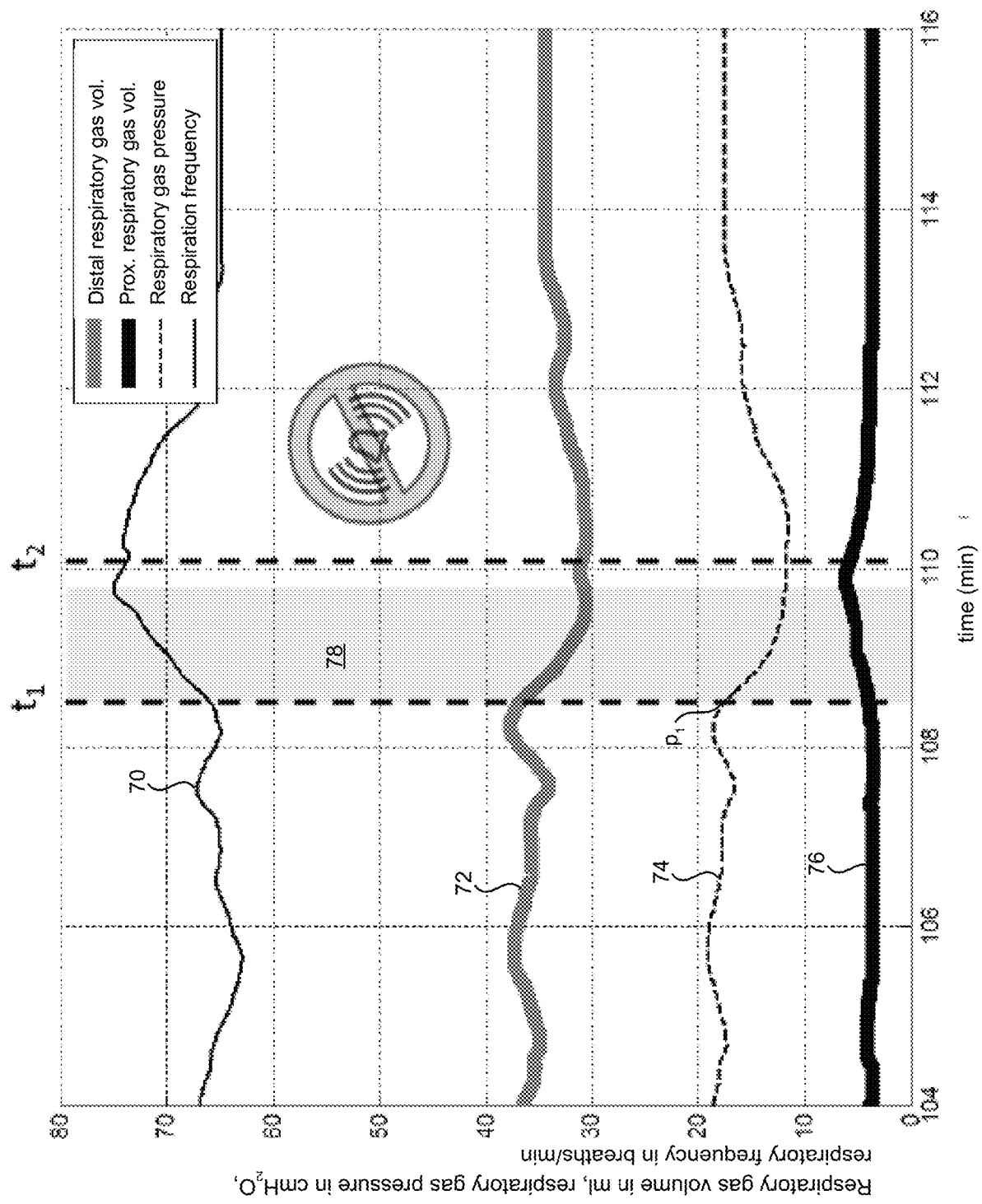
FIG. 4 shows exemplifying clinical curves, plotted over time, for the respiration frequency of the patient, distal respiratory gas volume, proximal respiratory gas volume, and respiratory gas pressure, in the context of a candidate fault that has been identified but rejected.

FIG. 4 shows a first diagram in which the respiration frequency is plotted as breaths per minute as graph 70; the distal respiratory gas volume, i.e. the integral over time of the respiratory gas flow measured by distal flow sensor 48, in milliliters, is plotted as curve 72; the respiratory gas pressure, in centimeters of water column, is plotted as curve 74; and lastly the proximal respiratory gas volume, i.e. the integral over time of the respiratory gas flow measured by proximal flow sensor 44, again in milliliters, is plotted as curve 76.

As discussed in the introduction to the description, a quantitative difference usually exists between the distal respiratory gas volume in accordance with curve 72 and the proximal respiratory gas volume in accordance with curve 76, due to elasticity in ventilation conduit arrangement 30 and due to leakage flows (cross-flows) in the region of the valve arrangement, so that a portion of the respiratory gas flow in the ventilation conduit arrangement can flow via Y-connection piece 45 directly from inhalation valve 20 to exhalation valve 22 without reaching patient 12.

As a rule, the quantitative difference between the distal and proximal respiratory gas volumes is known, or a volume difference value permissibility range is defined for that quantitative difference. As long as the quantitative difference between the distal and proximal respiratory gas volumes lies within that permissibility range, there is no reason to assume a malfunction of the ventilation apparatus, in particular of proximal flow sensor 44.

When the quantitative difference between the distal and proximal respiratory gas volumes departs from the associated permissibility range, however, this could be due to a functional impairment in proximal flow sensor 44, so that when the aforesaid volume difference value departs from the associated permissibility range, control device 18 sets a candidate fault flag and thus identifies a candidate fault. In FIG. 4 this occurs, for example, at time $t_1$.

Be it noted for clarification at this juncture that time $t_1$ does not need to be the only point in time in FIG. 4 at which control device 18 identifies a candidate for a fault in the proximal flow sensor. The candidate fault identified at time $t_1$ will, however, now be considered in further detail below. With the identification of the candidate fault at time $t_1$, the control device begins a verification phase that preferably continues over exactly 50 breaths. It ends at time $t_2$ in FIG. 4. It also stores the respiratory gas pressure (labeled "$p_1$" in FIG. 4) existing at time $t_1$ at which the candidate fault was identified. This value $p_1$ is the basis of a rejection criterion that will be discussed in further detail below in conjunction with FIG. 5.

When the verification phase begins at time $t_1$, control device 18 begins to investigate the breaths that occur as to whether they are active or mandatory breaths. It uses for that purpose the signal evaluation procedure presented in conjunction with FIG. 3. For the respiration events of FIG. 4, control device 18 ascertains that the entire gray-shaded region 78 exhibits active breaths. Because, at the end of the verification phase at time $t_2$, more than 50% of the (by definition) 50 breaths of the verification phase were active breaths, a rejection criterion is met and control device 18 rejects the candidate fault identified at time $t_1$ and does not carry out any further control actions on the basis of identification of the candidate fault. The background of this embodiment of control device 18 is that in the case in which more than half the breaths during the verification phase were active breaths, the reason for the decrease, at first assessed as being potentially critical, in the difference value between the distal and proximal respiratory gas volumes is the spontaneous respiration by patient 12 and not any fault in or damage to proximal flow sensor 44.

In the example of FIG. 4, for instance, the increase in the respiration frequency, beginning at time $t_1$, over the entire spontaneous respiration region 78 indicates that spontaneous respiration by the patient exists in region 78.

Figure 5:
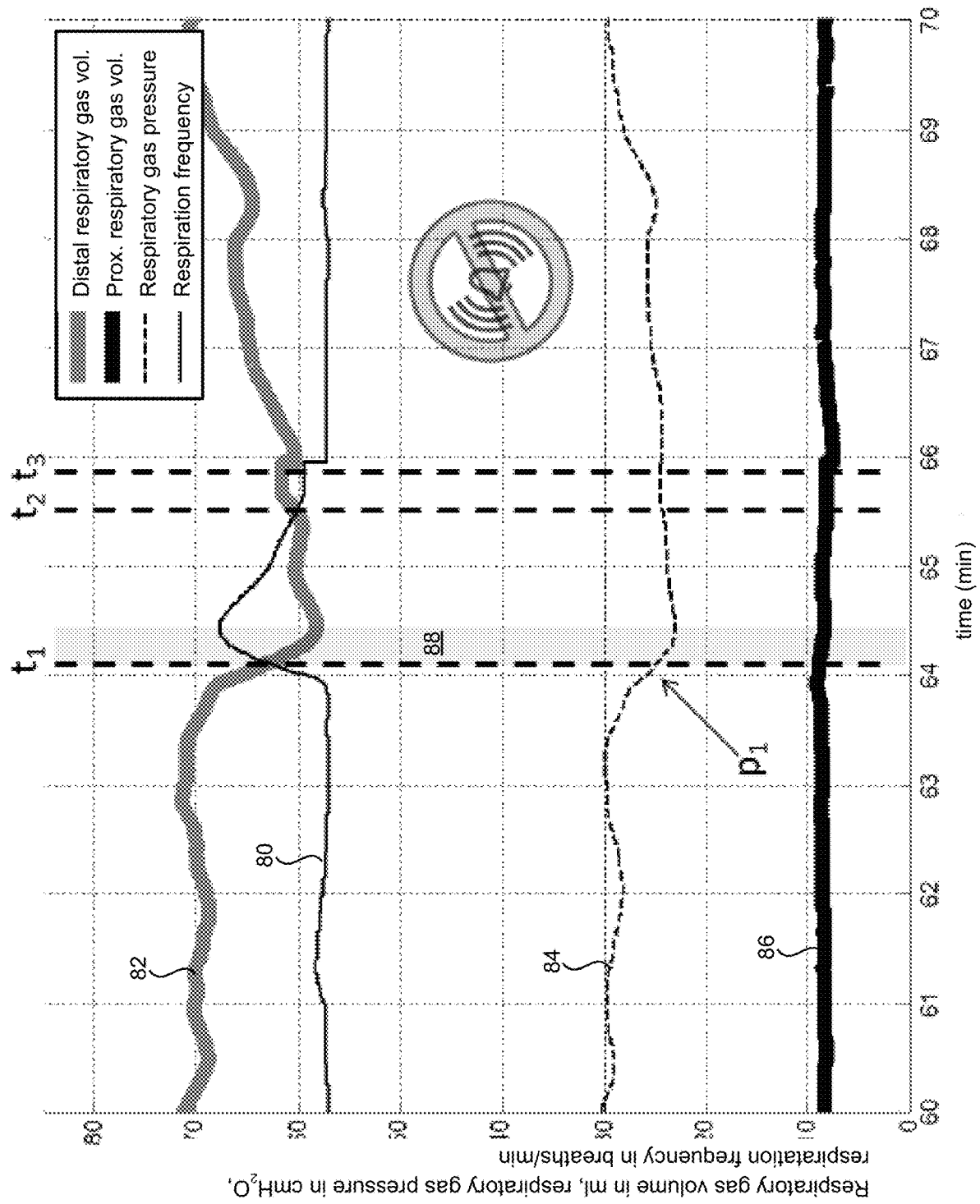
FIG. 5 is a diagram of the same parameters as in FIG. 4 plotted over time, with a candidate fault that was identified but was rejected for reasons other than those in the diagram of FIG. 4.

FIG. 5 is a diagram of a different but comparable respiration situation. Value curves that are the same as those in FIG. 4 are labeled in FIG. 5 with the same reference characters but incremented by 10. Once again, at time $t_1$ a quantitative difference value between the distal and proximal respiratory gas volumes (see curves 82 and 86 in FIG. 5) lies outside a permissibility range, so control device 18, which identifies the departure from the permissibility range, begins a verification phase. The respiratory gas pressure existing at the beginning of the verification phase, i.e. at time $t_1$ at which a candidate fault is identified, measured by a pressure sensor connected to proximal flow sensor 44, is stored in a data memory.

By the end of the verification phase (once again lasting 50 breaths) at time $t_2$, active breaths have occurred (see gray region 88 in FIG. 5) at the beginning of the verification phase, but considerably fewer than the active-breath threshold of 50% of the breaths, so that a rejection criterion relating to the occurrence of active breaths is not met. No other rejection criterion is met, for example that the difference value between the two respiratory gas volumes, or a quantitative difference value between the respiratory gas pressure at time $t_1$ when the candidate fault is identified and a subsequently occurring respiratory gas pressure, lies within a pressure difference value permissibility range.

But because some spontaneous respiration did occur in the verification phase, control device 18 extends verification phase 12 beyond time $t_2$ to include a predetermined additional verification phase that lasts until time $t_3$ and encompasses approximately 10 to 15 further breaths.

This means that a decision as to whether proximal flow sensor 44 is categorized as faulty is made only after the extended verification phase.

No further active breaths occur by the end of verification phase $t_3$, but the distal respiratory gas flow increases so that the quantitative difference value between the distal and proximal respiratory gas flows increases back into its permissibility range. A rejection criterion therefore exists at time $t_3$, and the candidate fault identified at time $t_1$ is rejected by control device 18. No further control action by control device 18 occurs on the basis of the candidate fault identified at time $t_1$.

Figure 6:
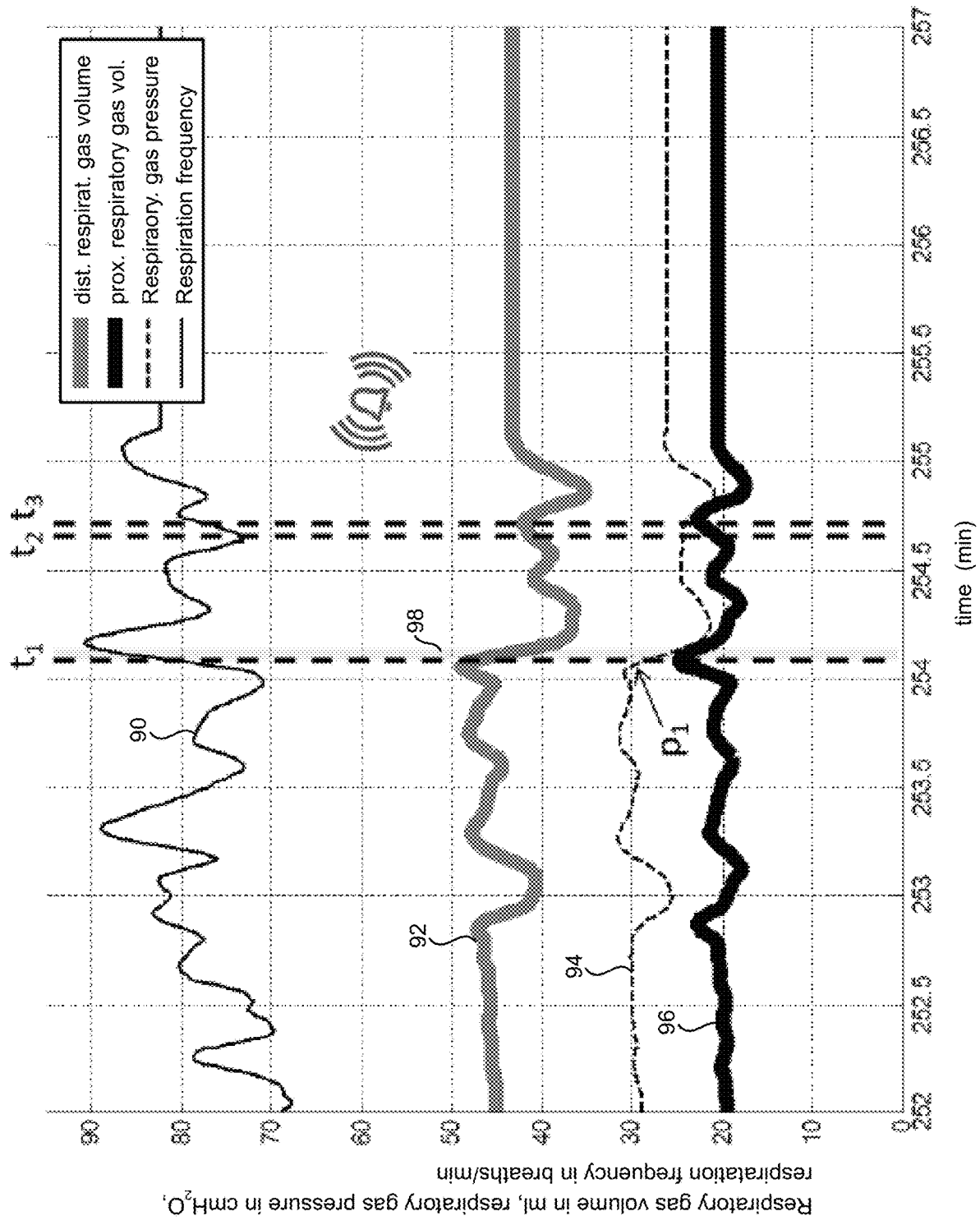
FIG. 6 is a third schematic diagram having the parameters of FIG. 5, with identification of a candidate fault and identification of a fault on that basis.

FIG. 6 is a diagram of a further respiration situation similar to that of FIGS. 4 and 5. Value curves that are the same as those in FIG. 5 are labeled with the same reference characters but incremented by 10.

Once again, at time $t_1$ (inter alia) a candidate for a fault in proximal flow sensor 44 is identified by control device 18, since the distal and proximal respiratory gas volumes are quantitatively approaching one another so closely that their difference value lies outside a predetermined permissibility range. At time $t_1$, control device 18 begins the predetermined verification phase in which control device 18 checks whether predetermined rejection criteria, which result in rejection of the candidate fault, exist or are occurring.

At the beginning of the verification phase, active breaths occur to a small extent, as indicated by the narrow gray region 98 that immediately follows time $t_1$ at which the candidate fault is detected. A rejection criterion has not occurred by time $t_2$ (the predefined end of the verification phase). But because some spontaneous respiration did occur in the verification phase, it is extended to include an additional verification phase until time $t_3$. The additional verification phase is shorter in the exemplifying embodiment of FIG. 6 than in the instance depicted in FIG. 5; this can be the result, for example, of differing patient data.

Because a rejection criterion has also not occurred by the end of the extended verification phase at time $t_3$, at time $t_3$ control device 18 infers a fault from the candidate fault identified at time $t_1$ and performs a control action, for example by the fact that the control device initiates an alarm together with a specific error message.

The invention claimed is:

1. A ventilation apparatus for artificial ventilation of a patient, comprising:
   a respiratory gas source; a ventilation conduit arrangement proceeding between the respiratory gas source and a patient-side proximal end;
   a valve arrangement having an inhalation valve and an exhalation valve;
   a flow sensor arrangement for quantitative detection of a gas flow in the ventilation conduit arrangement having a distal flow sensor arranged farther from the patient-side end of the ventilation conduit arrangement and a proximal flow sensor located closer to the patient-side end of the ventilation conduit arrangement;
   a pressure sensor arrangement for quantitative detection of a gas pressure of gas flowing in the ventilation conduit arrangement; a pressure modification arrangement for modifying the gas pressure of the gas flowing in the ventilation conduit arrangement;
   a control device that is configured to at least to control the operation of the pressure modification arrangement on the basis of measured signals of the proximal flow sensor, and to determine a fault in the proximal flow sensor as a function of measured signals of the proximal flow sensor and of the distal flow sensor;
   wherein the control device is configured to determine, as a function of measured signals of the proximal flow sensor and of the distal flow sensor, the proximal flow sensor measuring a candidate fault, and to determine a fault in the proximal flow sensor only with a time delay after identification of the candidate fault, the control device being configured to reject the candidate fault in the instance, during a verification phase that begins with or after identification of the candidate fault, at least one rejection criterion, taking into account a degree of spontaneous respiration activity by the patient, for rejecting the candidate fault is met; wherein the control device is configured to determine said fault only from the candidate fault that is not rejected during the verification phase.

2. The ventilation apparatus according to claim 1, wherein the at least one rejection criterion includes a number of active breaths by the patient being ventilated with the ventilation apparatus which are initiated by the patient during the verification phase exceeds an active-breath threshold value.

3. The ventilation apparatus according to claim 2, wherein the control device is configured to identify an active breath.

4. The ventilation apparatus according to claim 3, wherein the control device is configured to detect a time period detection value, which represents a time period between the initiation of a detected breath and the initiation of the breath immediately following initiation of the detected breath, as a breath duration of the detected breath, and to compare the time period detection value with an operating time period value that represents a time period between the respective mandatory initiations of two immediately successive mandatory breaths initiated by the ventilation apparatus, constituting a mandatory breath duration, the control device being configured to identify the detected breath, on the basis of the time period comparison result, as an active breath.

5. The ventilation apparatus according to claim 3, wherein the control device is configured to detect a time period detection value, which represents a time period between the initiation of a detected breath and the initiation of the breath immediately following the detected breath, as a breath duration of the detected breath, and to compare the detected value with a time period comparison value that represents an average value of breath durations averaged over a plurality of breaths, the control device being configured to identify the detected breath as an active breath on the basis of the time period comparison result.

6. The ventilation apparatus according to claim 5, wherein the time period comparison value reproduces a sliding average of breath durations over a predetermined number of breaths following one another until the detected breath.

7. The ventilation apparatus according to claim 3, wherein the control device is configured to detect a gas pressure of gas flowing in the ventilation conduit arrangement and to compare a gas pressure detected during a detected breath with the gas pressure detected during a preceding breath, the control device being configured to identify the detected breath as an active breath on the basis of the pressure comparison result.

8. The ventilation apparatus according to claim 3, wherein the control device is configured to detect, during a detected breath, at least one value of an esophageal pressure and of a pleural pressure of the patient, and to identify the detected breath as an active breath on the basis of the at least one detected pressure value.

9. The ventilation apparatus according to claim 2, wherein the active breath threshold value is equal to at least 39% of the total number of breaths in the verification phase.

10. The ventilation apparatus according to claim 2, wherein the control device is configured to extend the verification phase to include an additional verification phase when the number of active breaths ascertained during the predetermined verification phase is greater than zero and less than the predetermined active breath threshold value.

11. The ventilation apparatus according to claim 1, wherein the at least one rejection criterion additionally includes at least one of a quantitative volume difference value, which indicates a difference between the distal gas volume ascertained by means of the distal flow sensor and the proximal gas volume ascertained by means of the proximal flow sensor during the same breath, lies within a volume difference value permissibility range and a quantitative pressure difference value, which indicates a difference between the gas pressures detected by the pressure sensor arrangement during different breaths, lies within a pressure difference value permissibility range.

12. The ventilation apparatus~ according to claim 1, wherein the control device is configured to control the pressure modification arrangement in a mandatory ventilation operating mode as intended, to modify the gas pressure of the gas flowing in the ventilation conduit arrangement on the basis of the measured signal of the proximal flow sensor in such a way that a gas volume value ascertained on the basis of the gas flow value detected by the proximal flow sensor lies within a predefined volume value range.

13. The ventilation apparatus according to claim 1, wherein the proximal flow sensor is a differential pressure sensor the pressure sensor arrangement detecting at least one of the gas pressures detected at the differential pressure sensor as the gas pressure of gas flowing in the ventilation conduit arrangement; and wherein the control device uses that detected gas pressure to ascertain a candidate fault in the proximal flow sensor.

14. The ventilation apparatus according to claim 1, wherein the control device is configured to perform a control action on the ventilation apparatus when the control device determines fault in the proximal flow sensor.

15. The ventilation apparatus according to claim 1, wherein the control device is configured to control the pressure modification arrangement, in a mandatory ventilation operating mode as intended, to modify the gas pressure of the gas flowing in the ventilation conduit arrangement on the basis of the measured signal of the proximal flow sensor in such a way that a gas volume value ascertained on the basis of the gas flow value detected by the proximal flow sensor lies within a predefined volume value range, and is substantially constant.

16. The ventilation apparatus according to claim 1, wherein the control device is configured to perform a control action on the ventilation apparatus to output a fault message or an alarm, when the control device determines a fault in the proximal flow sensor.

17. The ventilation apparatus according to claim 2, wherein the active breath threshold value is equal to at least 45% of the total number of breaths in the verification phase.

18. The ventilation apparatus according to claim 2, wherein the active breath threshold value is equal to at least 50% of the total number of breaths in the verification phase.

* * * * *